(12) United States Patent
Riedel et al.

(10) Patent No.: US 6,218,489 B1
(45) Date of Patent: Apr. 17, 2001

(54) POLYMERIZATION PROCESS USING A MONOCYCLOPENTADIENYL COMPOUND AS A CATALYST COMPONENT

(75) Inventors: Michael Riedel, Essen; Gerhard Erker; Lothar Duda, both of Münster, all of (DE)

(73) Assignee: Targor GmbH (DE)

( * ) Notice: Subject to any disclaimer, the term of this patent is extended or adjusted under 35 U.S.C. 154(b) by 0 days.

(21) Appl. No.: 09/238,992

(22) Filed: Jan. 28, 1999

Related U.S. Application Data

(62) Division of application No. 08/877,832, filed on Jun. 18, 1997, now Pat. No. 6,090,739.

(30)  Foreign Application Priority Data

Jun. 20, 1996 (DE) ............................................. 196 24 581

(51) Int. Cl.$^7$ ................................ C08F 4/44; C08F 4/642
(52) U.S. Cl. ...................... 526/161; 526/127; 526/129; 526/134; 526/161; 526/172; 526/943
(58) Field of Search ..................................... 526/127, 129, 526/134, 161, 172, 943

(56)  References Cited

U.S. PATENT DOCUMENTS

| | | | |
|---|---|---|---|
| 5,026,625 | 6/1991 | Riediker et al. ..................... | 430/281 |
| 5,504,169 | * 4/1996 | Canich ................................ | 526/127 |
| 5,723,399 | * 3/1998 | Takemoto et al. .................... | 502/113 |
| 6,107,232 | * 8/2000 | Yokota ................................ | 502/155 |

FOREIGN PATENT DOCUMENTS

| | | |
|---|---|---|
| 42 18 199 | 12/1993 | (DE) . |
| 318 893 | 11/1988 | (EP) . |
| 416 815 | 8/1990 | (EP) . |
| 495 375 | 1/1992 | (EP) . |
| 514 828 | 5/1992 | (EP) . |

\* cited by examiner

*Primary Examiner*—Bernard Lipman
*Assistant Examiner*—R. Rabago
(74) *Attorney, Agent, or Firm*—Connolly Bove Lodge & Hutz LLP

(57)  ABSTRACT

The present invention relates to a process to prepare an olefin using a transition metal compound of the formula I as a catalyst component

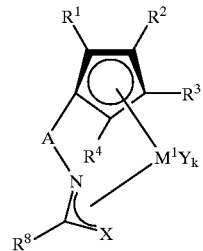

where $M^1$ is a metal of group IIIb, IVb or Vb of the Periodic Table of the Elements, $R^1$, $R^2$, $R^3$ and $R^4$ are identical or different and are each a hydrogen atom or a substituent, $R^5$ are identical or different and are a substituent, Y are identical or different and are each a hydrogen atom, a $C_1$–$C_{40}$-hydrocarbon-containing group, an OH group, a halogen atom or an $NR^5{}_2$ group, where $R^5$ are identical or different and are each a halogen atom, a $C_1$–$C_{10}$-alkyl group or a $C_6$–$C_{10}$-aryl group, k is an integer which corresponds to the valence of the transition metal atom $M^1$ minus two and if Y is a butadiene unit, k is 1, A is a bridge.

$R^8$ is a hydrogen atom, a halogen atom, a $C_1$–$C_{40}$-group, an —$SiR^5{}_3$, —$NR^5{}_2$, —$Si(OR^5)_3$, —$Si(SR^5)_3$ or —$PR^5{}_2$ radical, where $R^5$ are identical or different and are each a halogen atom, a $C_1$–$C_{10}$-alkyl group or a $C^6$–$C_{10}$-alkyl group or a $C_6$–$C_{10}$-aryl group, and X is an element of group Va or VIa of the Periodic Table of the Elements, where if X is an element of group Va, X bears a radical $R^9$ which is a hydrogen atom, a halogen atom, a $C_x$–$C_{40}$-group, an —$SiR^5{}_3$, —$NR^5{}_2$, —$Si(OR^5)_3$, —$Si(SR^5)_3$ or —$PR^5{}_2$ radical, where $R^5$ are identical or different and are each a halogen atom, a $C_1$–$C_{10}$-alkyl group or a $C_6$–$C_{10}$-aryl group.

13 Claims, No Drawings

POLYMERIZATION PROCESS USING A MONOCYCLOPENTADIENYL COMPOUND AS A CATALYST COMPONENT

This application is a divisional of Ser. No. 80/877,832, which was filed on Jun. 18, 1997, now U.S. Pat No. 6,090,739.

The present invention relates to a transition metal compound and a process for its preparation and also its use as a catalyst component in the preparation of polyolefins.

The preparation of polyolefins using soluble metallocenes or monocyclopentadienyl compounds in combination with aluminoxanes or other cocatalysts which, owing to their Lewis acidity, can convert the neutral transition metal compound into a cation and stabilize it is known from the literature (EP-A 129 368, EP-A 351 392, EP-A 416 815).

Metallocenes and monocyclopentadienyl compounds are of great interest not only in respect of the polymerization or oligomerization of olefins. They can also be used as hydrogenation, epoxidation, isomerization and C—C coupling catalysts (Chem. Rev. 1992, 92, 965–994).

Use of soluble metallocene compounds based on bis(cyclopentadienyl)zirconium dialkyls or dihalides in combination with oligomeric aluminoxanes gives atactic polymers which, owing to their unbalanced and unsatisfactory product properties, are of little industrial importance. In addition, certain olefin copolymers are not obtainable.

Derivatives of zirconocene dichloride in which the two substituted cyclopentadienyl groups are connected to one another via a methylene, ethylene or dimethylsilyl bridge can, owing to their conformational rigidity, be used as catalysts for the isospecific polymerization of olefins (EP-A 316 155).

It is an object of the invention to provide new transition metal compounds.

The present invention accordingly provides a transition metal compound containing as ligands a cyclopentadienyl group and a further π-bonded unit which are connected to one another via a bridge A.

The transition metal compound of the invention has the formula I,

Formula I

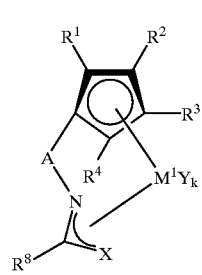

where $M^1$ is a metal of group IIIb, IVb or Vb of the Periodic Table of the Elements, $R^1$, $R_2$, $R^3$ and $R^4$ are identical or diferent and are each a hydrogen atom, a halogen atom, a $C_1$–$C_{40}$-hydrocarbon-containing group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl group or a $C_8$–$C_{40}$-arylalkenyl group, an —$SiR^5{}_3$, —$NR^5{}_2$, —$Si(OR^5)_3$, —$Si(SR^5)_3$ or —$PR^5{}_2$ radical, where $R^5$ are identical or different and are each a halogen atom, a $C_1$–$C_{10}$-alkyl group or a $C_6$–$C_{10}$-aryl group, or two or more radicals $R^1$, $R^2$, $R^3$ or $R^4$ together with the atoms connecting them form a ring system which preferably contains from 4 to 40, particularly preferably from 6 to 20, carbon atoms, Y are identical or different and are each a hydrogen atom, a $C_1$–$C_{40}$-hydrocarbon-containing group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl group, a $C_8$–$C_{40}$-arylalkenyl group, or a substituted or unsubstituted butadiene unit, an OH group, a halogen atom or a $NR^5{}_2$ group, where $R^5$ are identical or different and are each a halogen atom, a $C_1$–$C_{10}$-alkyl group or a $C_6$–$C_{10}$-aryl group, k is an integer which corresponds to the valence of the transition metal atom $M^1$ minus two and if Y is a butadiene unit, k is 1, A is a bridge such as

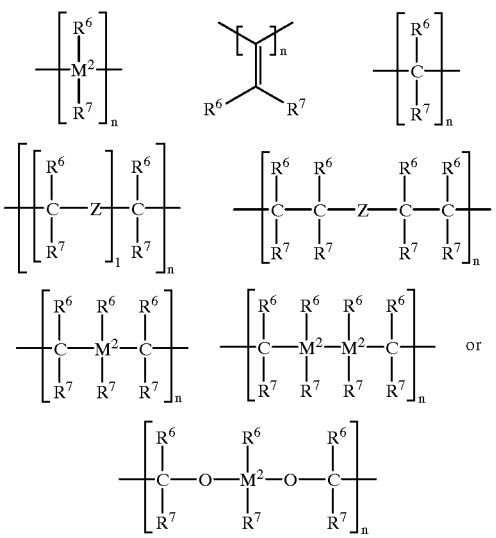

where n is an integer from 1 to 20, I is an integer from 1 to 20, Z is

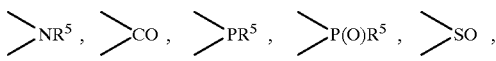

$SO_2$, O or S, where $R^5$ are identical or different and are each a halogen atom, a $C_1$–$C_{10}$-alkyl group or a $C_6$–$C_{10}$-aryl group, $R^6$ and $R^7$ are identical or different and are each a hydrogen atom, a halogen atom, a $C_1$–$C_{40}$-hydrocarbon-containing group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl group or a $C_8$–$C_{40}$-arylalkenyl group, or in each case two radicals $R^6$, in each case two radicals $R^7$, or one of each of the radicals $R^6$ and $R^7$ in each case together with the atoms connecting them form a ring system and $M^2$ is silicon, germanium or tin, $R^8$ is a hydrogen atom, a halogen atom, a $C_1$–$C_{40}$-group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl group or a $C_8$–$C_{40}$-arylalkenyl group, a —$SiR^5{}_3$, —$NR^5{}_2$, —$Si(OR^5)_3$, —$Si(SR^5)_3$ or —$PR^5{}_2$ radical, where $R^5$ are identical or different and are each a halogen atom, a $C_1$–$C_{10}$-alkyl group or a $C_6$–$C_{10}$-aryl group, and X is an element of group Va or VIa of the Periodic Table of the Elements, where if X is an element of group Va, X bears a radical $R^9$ which is a hydrogen atom, a halogen atom, a $C_1$–$C_{40}$-group such as a $C_1$–$C_{20}$-alkyl group, a $C_1$–$C_{10}$-alkoxy group, a $C_6$–$C_{20}$-aryl group, a $C_2$–$C_{12}$-alkenyl group, a $C_7$–$C_{40}$-alkylaryl group or a $C_8$–$C_{40}$-arylalkenyl group, an —$SiR^5_3$, —$NR^5_2$, —$Si(OR^5)_3$, —$Si(SR^5)_3$ or —$PR^5_2$ radical, where $R^5$ are identical or different and are each a halogen atom, a $C_1$–$C_{10}$-alkyl group or a $C_6$–$C_{10}$-aryl group.

For compounds of the formula I, it is preferred that $M^1$ is a metal of group IVb of the Periodic Table of the Elements, for example titanium, zirconium or hafnium, $R^1$, $R^2$, $R^3$ and $R^4$ are identical or different and are each a hydrogen atom or a $C_1$–$C_{10}$-hydrocarbon-containing group such as a $C_1$–$C_{10}$-alkyl group or a $C_6$–$C_{10}$-aryl group, or two or more radicals $R^1$, $R^2$, $R^3$ or $R^4$ together with the atoms connecting them form a ring system which preferably has from 6 to 10 carbon atoms, Y are identical and, in particular, are each a $C_1$–$C_{10}$-hydrocarbon-containing group such as a $C_1$–$C_4$-alkyl group or a substituted or unsubstituted, in particular unsubstituted, butadiene unit, or a halogen atom, in particular chlorine, A is

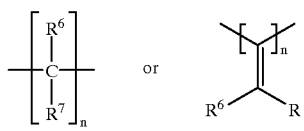

where n is an integer from 1 to 8, in particular 1, 2, 3 or 4, $R^6$ and $R^7$ are identical or different and are each a hydrogen atom or a $C_1$–$C_{10}$-hydrocarbon-containing group such as a $C_1$–$C_{10}$-alkyl group or a $C_6$–$C_{10}$-aryl group, or in each case two radicals $R^6$, in each case two radicals $R^7$, or one of each of the radicals $R^6$ and $R^7$ in each case together with the atoms connecting them form a hydrocarbon ring system, $R^8$ is a $C_1$–$C_{10}$-hydrocarbon group such as a $C_1$–$C_4$-alkyl group or a $C_6$–$C_{10}$-aryl group, and X is an element of group Va, in particular nitrogen or phosphorus, or group VIa, in particular oxygen or sulfur, of the Periodic Table of the Elements, where if X is an element of group Va, X bears a radical $R^9$ which is a hydrogen atom, a $C_1$–$C_{10}$-hydrocarbon-containing group such as a $C_1$–$C_{10}$-alkyl group or a $C_6$–$C_{10}$-aryl group or a —$SiR^5_3$, —$NR^5_2$, —$Si(OR^5)_3$, —$Si(SR^5)_3$ or —$PR^5_2$ radical, where $R^5$ are identical or different and are each a $C_1$–$C_{10}$-alkyl group or a $C_6$–$C_{10}$-aryl group.

Particular preference is given to compounds of the formula I in which $M^1$ is titanium or zirconium, $R^1$, $R^2$, $R^3$ and $R^4$ are identical or different and are each a hydrogen atom, a $C_1$–$C_4$-alkyl group such as methyl, ethyl, propyl, isopropyl, butyl, isobutyl or a $C_6$–$C_{10}$-aryl group such as phenyl or naphthyl, or $R^1$ and $R^2$ or $R^3$ and $R^4$ or $R^2$ and $R^3$ together with the atoms connecting them form an aromatic hydrocarbon ring system, in particular a six-membered ring, which may in turn be substituted, Y are identical and are, in particular, methyl, phenyl or chlorine, A is

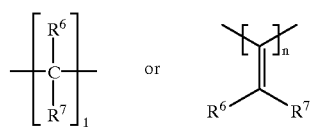

$R^6$ and $R^7$ are identical or different and are each a hydrogen atom, a $C_1$–$C_4$-alkyl group such as methyl, ethyl, propyl, isopropyl, butyl, isobutyl or a $C_6$–$C_{10}$-aryl group such as phenyl or naphthyl, $R^8$ is a $C_1$–$C_4$-alkyl group such as methyl, ethyl, propyl, isopropyl, butyl, isobutyl or a $C_6$–$C_{10}$-aryl group such as phenyl or naphthyl, and X is nitrogen or oxygen, where if X is nitrogen it bears a radical $R^9$ which is a hydrogen atom, a $C_1$–$C_4$-alkyl group such as methyl, ethyl, propyl, isopropyl, butyl, isobutyl or a $C_6$–$C_{10}$-aryl group such as phenyl or naphthyl, —$SiR^5_3$ or —$Si(OR^5)_3$, in particular —$SiR^5_3$, where $R^5$ are identical or different and are each a $C_1$–$C_4$-alkyl group such as methyl, ethyl, propyl, isopropyl, butyl, isobutyl or a $C_6$–$C_{10}$-aryl group such as phenyl or naphthyl.

The nomenclature is illustrated by the following transition metal compound:

(tert-butyl-$\eta^3$-amidato)-($\eta^5$-3-methylcyclopentadienyl)-2-phenyl-2,2-ethanediyl-zirconium dichloride

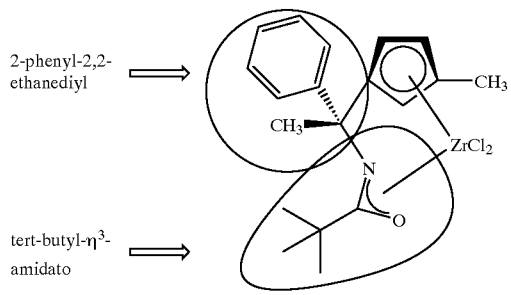

Examples of transition metal compounds of the invention are:

(tert-butyl-$\eta^3$-amidato)-($\eta^5$-cyclopentadienyl)-2,2-propanediyl-zirconium dichloride (phenyl-$\eta^3$-amidato)-($\eta^5$-cyclopentadienyl)-2,2-propanediyl-zirconium dichloride (methyl-$\eta^3$-amidato)-($\eta^5$-cyclopentadienyl)-2,2-propanediyl-zirconium dichloride (tert-butyl-$\eta^3$-amidato)-($\eta^5$-cyclopentadienyl)-2-phenyl-2,2-ethanediyl-titanium dichloride (phenyl-$\eta^3$-amidato)-($\eta^5$-cyclopentadienyl)-2-phenyl-2,2-ethanediyl-titanium dichloride (methyl-$\eta^3$-amidato)-($\eta^5$-cyclopentadienyl)-2-phenyl-2,2-ethanediyl-titanium dichloride (tert-butyl-$\eta^3$-amidato)-($\eta^5$-cyclopentadienyl)-2,2-ethenediyl-zirconium dichloride (phenyl-$\eta^3$-amidato)-($\eta^5$-cyclopentadienyl)-2,2-ethenediyl-zirconium dichloride (methyl-$\eta^3$-amidato)-($\eta^5$-cyclopentadienyl)-2,2-ethenediyl-zirconium dichloride (p-tolyl-$\eta^3$-amidato)-($\eta^5$-cyclopentadienyl)-2,2-ethenediyl-zirconium dichloride (p-tolyl-$\eta^3$-amidato)-($\eta^5$-cyclopentadienyl)-2,2-ethenediyl-titanium dichloride (tert-butyl-η³-amidato)-(η⁵-indenyl)-2,2-propanediyl-zirconium dichloride
(phenyl-η³-amidato)-(η⁵-indenyl)-2-phenyl-2,2-ethanediyl-zirconium dichloride
(methyl-η³-amidato)-(η⁵-indenyl)-2,2-propanediyl-titanium dichloride
(tert-butyl-η³-amidato)-(η⁵-3-methylcyclopentadienyl)-2-phenyl-2,2-ethanediyl-titanium dichloride
(phenyl-η³-amidato)-(η⁵-3-methylcyclopentadienyl)-2-phenyl-2,2-ethanediyl-zirconium dichloride
(methyl-η³-amidato)-(η⁵-3-methylcyclopentadienyl)-2,2-propanediyl-titanium dichloride
(tert-butyl-N-methyl-η³-η-amidinato)-(η⁵-cyclopentadienyl)-2,2-propanediyl-zirconium dichloride which corresponds to the following structure

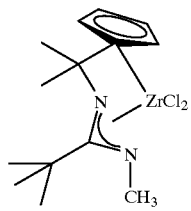

(phenyl-N-phenyl-η³-amidinato)-(η³-cyclopentadienyl)-2,2-propanediyl-zirconium dichloride
(methyl-N-trimethylsilyl-η³-amidinato)-(η⁵-cyclopentadienyl)-2,2-propanediyl-zirconium dichloride
(tert-butyl-N-methyl-η³-amidinato)-(η⁵-cyclopentadienyl)-2-phenyl-2,2-ethanediyl-titanium dichloride
(phenyl-N-trimethylsilyl-η³-amidinato)-(η⁵-cyclopentadienyl)-2-phenyl-2,2-ethanediyl-titanium dichloride
(methyl-N-phenyl-η³-amidinato)-(η⁵-cyclopentadienyl)-2-phenyl-2,2-ethanediyl-titanium dichloride
(tert-butyl-N-methyl-η³-amidinato)-(η⁵-cyclopentadienyl)-2,2-ethenediyl-zirconium dichloride
(phenyl-N-phenyl-η³-amidinato)-(η³-cyclopentadienyl)-2,2-ethenediyl-zirconium dichloride
(methyl-N-trimethylsilyl-η³-amidinato)-(η⁵-cyclopentadienyl)-2,2-ethenediyl-zirconium dichloride
(tert-butyl-N-trimethylsilyl-η³-amidinato)-(η⁵-indenyl)-2,2-propanediyl-zirconium dichloride
(phenyl-N-methyl-η³-amidinato)-(η⁵-indenyl)-2-phenyl-2,2-ethanediyl-zirconium dichloride
(methyl-N-phenyl-η³-amidinato)-(η⁵-indenyl)-2,2-propanediyl-titanium dichloride
(tert-butyl-η³-amidinato)-(η⁵-3-methylcyclopentadienyl)-2-phenyl-2,2-ethanediyl-titanium dichloride
(phenyl-η³-amidinato)-(η⁵-3-methylcyclopentadienyl)-2-phenyl-2,2-ethanediyl-zirconium dichloride
(methyl-η³-amidinato)-(η⁵-3-methylcyclopentadienyl)-2,2-propanediyl-titanium dichloride
(tert-butyl-η³-amidato)-(η⁵-fluorenyl)-2,2-propanediyl-zirconium dichloride
(phenyl-η³-amidato)-(η⁵-fluorenyl)-2-phenyl-2,2-ethanediyl-titanium dichloride
(methyl-η³-amidato)-(η⁵-fluorenyl)-2,2-ethenediyl-zirconium dichloride
(tert-butyl-N-methyl-η³-amidinato)-(η⁵-fluorenyl)-2,2-propanediyl-zirconium dichloride
(phenyl-N-trimethylsilyl-η³-amidinato)-(η⁵-fluorenyl)-2-phenyl-2,2-ethanediyl-titanium dichloride
(methyl-N-trimethylsilyl-η³-amidinato)-(η⁵-fluorenyl)-2,2-ethenediyl-zirconium dichloride
[(tert-butyl-η³-amidato)(dimethyl)(η⁵-fluorenyl)silanediyl] zirconium dichloride which corresponds to the following structure

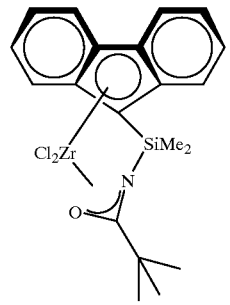

[(phenyl-η³-amidato)(methylphenyl)(η⁵-cyclopentadienyl)silanediyl]zirconium dichloride,
[(menthyl-η³-amidato)(diphenyl)(η⁵-indenyl)silanediyl] zirconium dichloride,
[(tert-butyl-N-menthyl-η³-amidinato)(dimethyl)(η⁵-cyclopentadienyl)silanediyl zirconium dichloride,
[(phenyl-N-trimenthylsilyl-η³-amidinato)(methylphenyl)(η⁵-indenyl)silanediyl]zirconium dichloride,
[(methyl-N-trimethylsilyl-η³-amidinato)(diphenyl)(η⁵-fluorenyl)silanediyl]zirconium dichloride,
(tert-butyl-η³-amidato)-η⁵-cyclopentadienyl)-1,1-vinylidenediyl-zirconium bis(diethylamide) which corresponds to following structure

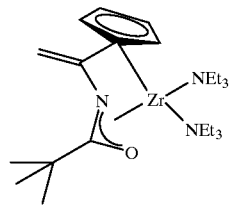

(tert-butyl-η³-amidato)-η⁵-cyclopentadienyl)-1,1-vinylidenediyl-zirconium bis(dimethylamide)
(p-tolyl-η³-amidato)-η⁵-cyclopentadienyl)-1,1-vinylidenediyl-zirconium bis(diethylamide)

The preparation of the transition metal compound of the invention is illustrated by the following reaction scheme.

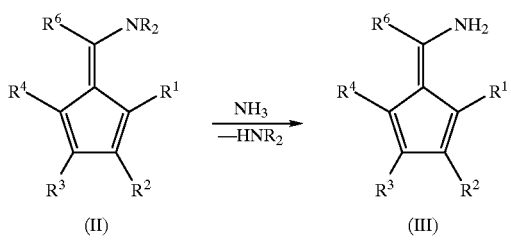

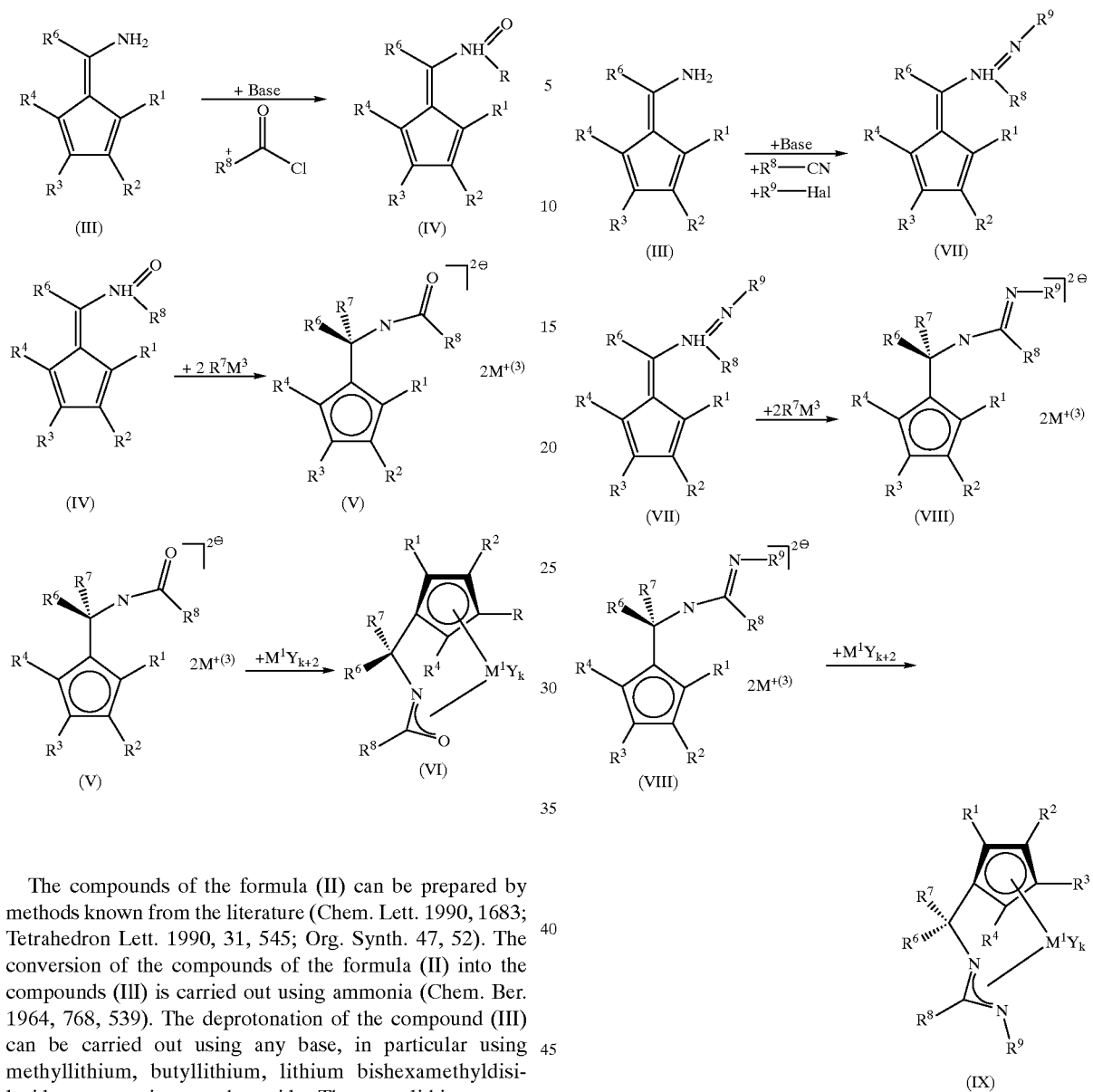

The compounds of the formula (II) can be prepared by methods known from the literature (Chem. Lett. 1990, 1683; Tetrahedron Lett. 1990, 31, 545; Org. Synth. 47, 52). The conversion of the compounds of the formula (II) into the compounds (III) is carried out using ammonia (Chem. Ber. 1964, 768, 539). The deprotonation of the compound (III) can be carried out using any base, in particular using methyllithium, butyllithium, lithium bishexamethyldisilazide or potassium tert-butoxide. The monolithium compound formed by this deprotonation can be reacted with acid chlorides or with nitrites so that the compounds (IV) or (VII) can be generated. The reaction of the compounds (IV) or (VII) with 2 equivalents of a nucleophilic and/or basic compound such as $R^7M^3$, where $M^3$ is a metal of group Ia or IIa of the Periodic Table of the Elements, leads to the formation of the corresponding compound (V) or (VIII). The subsequent reaction of the compound (V) or (VIII) in an inert solvent with the corresponding metal compound $M^1Y_{k+2}$, where k is an integer from 1 to 3 (e.g. vanadium trichloride, zirconium tetrachloride, niobium pentachloride), is known in principle and leads to the formation of the transition metal compound of the invention (VI) or (IX). Suitable inert solvents are aliphatic or aromatic solvents such as hexane or toluene, ether solvents such as tetrahydrofuran or diethyl ether or halogenated hydrocarbons such as methylene chloride or halogenated aromatic hydrocarbons such as o-dichlorobenzene.

The symbols used in the formulae II to IX are as defined for formula I.

The transition metal compounds of the invention are highly active catalyst components for olefin polymerization. Depending on the substitution pattern of the ligands, the transition metal compounds can be obtained as an isomer mixture. The transition metal compounds are preferably used in the form of pure isomers, but can also be used as an isomer mixture.

The present invention further provides a process for preparing a polyolefin by polymerization of one or more olefins in the presence of a catalyst system comprising at least one transition metal compound of the invention and at least one cocatalyst. For the purposes of the present invention, the term polymerization refers to either homopolymerization or copolymerization.

In the process of the invention, preference is given to polymerizing one or more olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins having 1–20 carbon atoms, e.g. ethylene, propene, 1-butene, 1-pentene, 1-hexene, 4-methyl-1-pentene or 1-octene, styrene, cyclic or acyclic dienes such as 1,3-butadiene, isoprene, 1,4-hexadiene, norbornadiene, vinylnorbornene, 5-ethylidenenorbornene or cyclic monoolefins such as norbornene or tetracyclododecene. In the process of the invention, preference is given to homopolymerizing ethylene or propylene or copolymerizing ethylene and propylene with one another and/or with one or more acyclic 1-olefins having from 4 to 20 carbon atoms and/or with one or more dienes having from 4 to 20 carbon atoms, e.g. 1,3-butadiene.

The polymerization is preferably carried out at a temperature of from −78 to 250° C., particularly preferably from 50 to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. Preferred embodiments are gas-phase polymerization and suspension polymerization.

The catalyst used in the process of the invention preferably comprises one transition metal compound. It is also possible to use mixtures of two or more transition metal compounds, e.g. for preparing polyolefins having a broad or multimodal molecular weight distribution.

A suitable cocatalyst in the process of the invention is in principle any compound which, owing to its Lewis acidity, can convert the neutral transition metal compound into a cation and stabilize it ("labile coordination"). In addition, the cocatalyst or the anion formed therefrom should undergo no further reactions with the cation formed (EP 427 697). The cocatalyst used is preferably an aluminum compound and/or a boron compound.

The boron compound preferably has the formula $R^{12}_x NH_{4-x} BR^{13}_4$, $R^{12}_x PH_{4-x} BR^{13}_4$, $R^{12}_3 CBR^{13}_4$ or $BR^{13}_3$, where x is a number from 1 to 4, preferably 3, the radicals $R^{12}$ are identical or different, preferably identical, and are $C_1$–$C_{10}$-alkyl or $C_6$–$C_{18}$-aryl or two radicals $R^{12}$ together with the atoms connecting them form a ring, and the radicals $R^{13}$ are identical or different, preferably identical, and are $C_6$–$C_{18}$-aryl which may be substituted by alkyl, haloalkyl or fluorine. In particular, $R^{12}$ is ethyl, propyl, butyl or phenyl and $R^{13}$ is phenyl, pentafluorophenyl, 3,5-bistrifluoromethylphenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula Xa for the linear type and/or the formula Xb for the cyclic type,

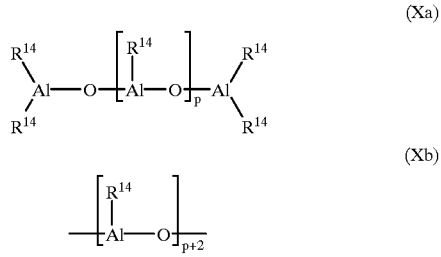

where, in the formulae Xa and Xb, the radicals $R^{14}$ are identical or different and are each hydrogen or a $C_1$–$C_{20}$-hydrocarbon group such as a $C_1$–$C_{18}$-alkyl group, a $C_6$–$C_{18}$-aryl group or benzyl and p is an integer from 2 to 50, preferably from 10 to 35.

Preferably, the radicals $R^{14}$ are identical and are hydrogen, methyl, isobutyl, phenyl or benzyl, particularly preferably methyl.

If the radicals $R^{14}$ are different they are preferably methyl and hydrogen or alternatively methyl and isobutyl, where hydrogen or isobutyl are preferably present in a numerical proportion of from 0.01 to 40% (of the radicals $R^{14}$).

The methods of preparing the aluminoxanes are known. The precise spatial structure of the aluminoxanes is not known (J. Am. Chem. Soc. (1993) 115, 4971). For example, it is conceivable that chains and rings join to form larger two-dimensional or three-dimensional structures.

Regardless of the method of preparation, all aluminoxane solutions have in common a varying content of unreacted aluminum starting compound which is present in free form or as adduct.

It is possible to preactivate the transition metal compound using a cocatalyst, in particular an aluminoxane, before use in the polymerization reaction. This significantly increases the polymerization activity. The preactivation of the transition metal compound is preferably carried out in solution. Here, the transition metal compound is preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The transition metal compound can be used in the same concentration, but it is preferably used in an amount of from $10^{-4}$ to 1 mol per mol of aluminoxane. The preactivation time is from 5 minutes to 60 hours, preferably from 5 to 60 minutes. The preactivation is carried out at a temperature of from −78 to 150° C., preferably from 0 to 80° C.

The transition metal compound is preferably employed in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other cocatalysts mentioned are used in approximately equimolar amounts to the transition metal compound. However, higher concentrations are also possible in principle.

The aluminoxane can be prepared in various ways by known methods. One of the methods is, for example, reacting an aluminum hydrocarbon compound and/or a hydridoaluminum hydrocarbon compound with water (gaseous, solid, liquid or bound—for example as water of crystallization) in an inert solvent (such as toluene). To prepare an aluminoxane having different radicals $R^{14}$, for example, two different trialkylaluminums corresponding to the desired composition are reacted with water.

To remove catalyst poisons present in the olefin, purification using an aluminum compound, preferably an aluminum alkyl such as trimethylaluminum or triethylaluminum, is advantageous. This purification can be carried out either in the polymerization system itself or the olefin is brought into contact with the aluminum compound and subsequently separated off again before addition to the polymerization system.

In the process of the present invention, hydrogen can be added as molecular weight regulator and/or to increase the catalyst activity. This enables low molecular weight polyolefins such as waxes to be obtained.

In the process of the present invention, the transition metal compound is preferably reacted with the cocatalyst outside the polymerization reactor in a separate step using a suitable solvent. Application to a support can be carried out during this step.

In the process of the invention, a prepolymerization can be carried out with the aid of the transition metal compound. For the prepolymerization, preference is given to using the (or one of the) olefin(s) used in the polymerization.

The catalyst used in the process of the invention can be supported. Application to a support enables, for example, the particle morphology of the polymer produced to be controlled. The transition metal compound can be reacted first with the support and subsequently with the cocatalyst. The cocatalyst can also first be supported and subsequently reacted with the transition metal compound. It is also possible to support the reaction product of transition metal compound and cocatalyst. Suitable support materials are, for example, silica gels, aluminum oxides, solid aluminoxane or other inorganic support materials such as magnesium chloride. Another suitable support material is a polyolefin powder in finely divided form. The preparation of a supported catalyst can be carried out, for example, as described in EP 567 952.

Preferably, the cocatalyst, e.g. aluminoxane, is applied to a support such as silica gels, aluminum oxides, solid aluminoxane, other inorganic support materials or a polyolefin powder in finely divided form and then reacted with the transition metal compound.

Inorganic supports used can be oxides which have been produced flame-pyrolyitcally by combustion of element halides in a hydrogen/oxygen flame or can be prepared as silica gels in particular particle size distributions and particle shapes.

The preparation of a supported cocatalyst can be carried out, for example, as described in EP 578 838 in the following manner in a stainless steel reactor in an explosion-proof design having a pressure rating of 60 bar and a pumped circulation system, with inert gas supply, cooling by means of jacket cooling and a second cooling circuit via a heat exchanger on the pumped circulation system. The pumped circulation system draws in the reactor contents via a connection in the bottom of the reactor by means of a pump and pushes them into a mixer and through a riser line via a heat exchanger back into the reactor. The mixture is configured such that in the inlet section there is a constricted pipe cross section where the flow velocity is increased and into the turbulence zone of which, axially and opposite to the flow direction, there is conducted a thin feed fine through which, pulsed, a defined amount of water under 40 bar of argon can be fed in. The reaction is monitored by means of a sampler on the pumped circuit. Other reactors are also suitable in principle.

Further ways of preparing a supported cocatalyst are described in EP 578 838. According to these, the transition metal compound of the invention is applied to the supported cocatalyst by stirring the dissolved transition metal compound with the supported cocatalyst. The solvent is removed and replaced by a hydrocarbon in which both cocatalyst and the transition metal compound are insoluble.

The reaction to form the supported catalyst system is carried out at a temperature of from −20 to +120° C., preferably from 0 to 100° C., particularly preferably from 15 to 40° C. The transition metal compound is reacted with the supported cocatalyst by combining a 1–40% by weight, preferably 5–20% by weight, suspension of the cocatalyst in an aliphatic, inert suspension medium such as n-decane, hexane, heptane or diesel oil with a solution of the transition metal compound in an inert solvent such as toluene, hexane, heptane or dichloromethane or with the finely milled solid of the transition metal compound. Conversely, a solution of the transition metal compound can also be reacted with the solid cocatalyst.

The reaction is carried out by intensive mixing, for example by stirring, at a molar $Al/M^1$ ratio of from 100/1 to 10000/1, preferably from 100/1 to 3000/1, and a reaction time of from 5 to 120 minutes, preferably from 10 to 60 minutes, particularly preferably from 10 to 30 minutes, under inert conditions.

During the course of the reaction time for preparing the supported catalyst system, particularly when using the transition metal compound of the invention having absorption maxima in the visible region, changes in color of the reaction mixture occur and these enable the progress of the reaction to be followed.

After the reaction time has elapsed, the supernatant solution is separated off, for example by filtration or decantation. The remaining solid is washed from 1 to 5 times with an inert suspension medium such as toluene, n-decane, hexane, diesel oil or dichloromethane to remove soluble constituents in the catalyst formed, in particular to remove unreacted and therefore soluble transition metal compound.

The supported catalyst system thus prepared can be resuspended as vacuum-dried powder or while still moist with solvent and metered as suspension in one of the abovementioned inert suspension media into the polymerization system.

If the polymerization is carried out as a suspension or solution polymerization, an inert solvent customary for the Ziegler low-pressure process is used. For example, the polymerization is carried out in an aliphatic or cycloaliphatic hydrocarbon; examples which may be mentioned are propane, butane, hexane, heptane, isooctane, cyclohexane and methylcyclohexane. It is also possible to use a petroleum or hydrogenated diesel oil fraction. Toluene can also be used. Preference is given to carrying out the polymerization in the liquid monomer.

Before addition of the catalyst, in particular the supported catalyst system (comprising a transition metal compound of the invention and a supported cocatalyst or comprising a transition metal compound of the invention and an organoaluminum compound on a polyolefin powder in finely divided form), another aluminum alkyl compound such as trimethylaluminum, triethylaluminum, triisobutylaluminum, trioctylaluminum or isoprenylaluminum can additionally be introduced into the reactor for making the polymerization system inert (for example to remove catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a small molar $Al/M^1$ ratio to be selected in the synthesis of a supported catalyst system.

If inert solvents are used, the monomers are metered in in gaseous or liquid form.

The time of the polymerization can be any desired, since the catalyst system to be used in the process of the invention displays only a small time-dependent drop in the polymerization activity.

The following examples serve to illustrate the invention.

Preparation and handling of organometallic compounds were carried out with exclusion of air and moisture under

EXAMPLE 1

(tert-Butyl-$\eta^3$-amidato)-($\eta^5$-cyclopentadienyl)-2,2-propanediyl-zirconium dichloride (1)

Synthesis of N-6-(6'-methylfulvenyl)pivalamide

While cooling in ice, 1 equivalent of pivalic chloride is added to a solution of 5.0 g (46.7 mmol) of 6-amino-6'-methylfulvene in 3 ml of triethylamine and 30 ml of tetrahydrofuran. The mixture is stirred for 24 hours and subsequently filtered. The filtrate is freed of the solvent and the residue is crystallized from diethyl ether.

$^1$H NMR (200 MHz, CDCl$_3$): 8.2 (s, 1H, NH); 6.6–6.3 (m, 4H, Cp-H); 2.7 (s, 3H, CH$_3$); 1.3 (s, 9H, CH$_3$).

Synthesis of (tert-butylamidato)(cyclopentadienyl)-2,2-propanediyl-dilithium

At –30° C., two equivalents of a methyllithium solution in diethyl ether (10 ml, 3.0 mmol) are added to a supension of 0.5 g of copper iodide in 50 ml of ether. The clear solution is warmed to 0° C. and 0.3 g (1.48 mmol) of N-6-(6'-methylfulvenyl)pivalamide in 50 ml of diethyl ether is subsequently added dropwise. The suspension is stirred for 24 hours, filtered and the solvent is removed under reduced pressure.

Synthesis of (tert-butyl-$\eta^3$-amidato)-($\eta^5$-cyclopentadienyl)-2,2-propanediyl-zirconium dichloride 0.3 g of (tert-butylamidato)(cyclopentadienyl)-2,2-propanediyl-dilithium (1.0 mmol) is suspended in diethyl ether and admixed with an equimolar amount of ZrCl$_4$ (0.35 g; 1.0 mmol). After a reaction time of 12 hours, the solvent is removed under reduced pressure and the residue is extracted with dichloromethane. The filtrate is evaporated to dryness and the compound (1) is obtained in a yield of 45%.

$^1$H NMR (200 MHz, C$_6$D$_6$): 5.8–5.4 (m, 4H, Cp-H); 1.6 (s, 3H, CH$_3$); 1.3 (s, 3H, CH$_3$); 1.2 (s, 9H, CH$_3$).

EXAMPLE 2

(tert-Butyl-$\eta^3$-amidato)-($\eta^5$-cyclopentadienyl)-2,2-ethenediyl-zirconium dichloride (2)

2 equivalents of lithium hexamethyldisilazane in 20 ml of diethyl ether are added dropwise to 0.38 g (2.0 mmol) of N-6-(6'-methylfulvenyl)pivalamide in 50 ml of diethyl ether. The suspension is stirred for 24 hours, filtered and the residue is washed with pentane.

Synthesis of (tert-butyl-$\eta^3$-amidato)-($\eta^5$-cyclopentadienyl)-2,2-ethenediyl-zirconium dichloride 0.3 g of (tert-butylamidato)(cyclopentadienyl)-2,2-ethenediyl-dilithium (1.0 mmol) is dissolved in tetrahydrofuran and admixed with an equimolar amount of ZrCl$_4$ (THF)$_2$ (0.35 g; 1.0 mmol). After a reaction time of 12 hours, the solvent is removed under reduced pressure and the residue is extracted with pentane. The filtrate is evaporated to dryness and the compound (2) is obtained in a yield of 74%.

$^1$H NMR (200 MHz, C$_4$D$_8$O): 6.4–5.8 (m, 4H, Cp-H); 4.8; 4.7 (each m, each 1H, CH); 1.1 (s, 9H, CH$_3$).

EXAMPLE 3

(p-Tolyl-$\eta^3$-amidato)-($\eta^5$-cyclopentadienyl)-2,2-ethenediyl-zirconium dichloride Synthesis of N-6-(6'-methylfulvenyl)-p-toluamide While cooling in ice, 1 equivalent of p-toluic chloride is added to a solution of 5.0 g (46.7 mmol) of 6-amino-6'-methylfulvene in 3 ml of triethylamine and 30 ml of tetrahydrofuran. The mixture is stirred for 24 hours and subsequently filtered. The filtrate is freed of the solvent and the residue is crystallized from diethyl ether.

$^1$H NMR (200 MHz, CDCl$_3$): 8.2 (s, 1H, NH); 7.7–7.0 (m, 4H, arom. H); 6.6–6.3 (m, 4H, Cp-H); 2.7 (s, 3H, CH$_3$); 2.3 (s, 3H, CH$_3$).

Synthesis of (p-tolylamidato)(cyclopentadienyl)-2,2-ethenediyl-dilithium 2 equivalents of lithium hexamethyldisilazide in 20 ml of diethyl ether are added dropwise to 0.38 g (2.0 mmol) of N-6-(6'-methylfulvenyl)-p-toluamide in 50 ml of diethyl ether. The suspension is stirred for 24 hours, filtered and the residue is washed with pentane.

Synthesis of (p-tolyl-$\eta^3$-amidato)-($\eta^5$-cyclopentadienyl)-2,2-ethenediyl-zirconium dichloride 0.3 g of (p-tolylamidato)-(cyclopentadienyl)-2,2-ethenediyl-dilithium (1.26 mmol) is dissolved in tetrahydrofuran and admixed with an equimolar amount of ZrCl$_4$ (THF)$_2$ (0.47 g; 1.26 mmol). After a reaction time of 12 hours, the solvent is removed under reduced pressure and the residue is extracted with pentane. The filtrate is evaporated to dryness and the compound C is obtained in a yield of 78%.

$^1$H NMR (200 MHz, C$_4$D$_8$O): 7.8–7.0 (m, 4H, arom. H); 6.6–5.9 (m, 4H, Cp-H); 4.9; 4.8 (each m, each 1H, CH); 2.3 (s, 3H, CH$_3$).

EXAMPLE 4

(p-Tolyl-$\eta^3$-amidato)-($\eta^5$-cyclopentadienyl)-2,2-ethenediyl-titanium dichloride Synthesis of (p-tolyl-$\eta^3$-amidato)-($\eta^5$-cyclopentadienyl)-2,2-ethenediyl-titanium dichloride 0.3 g of (p-tolylamidato)(cyclopentadienyl)-2,2-ethenediyl-dilithium (1.26 mmol) is dissolved in tetrahydrofuran and admixed with an equimolar amount of TiCl$_4$ (THF)$_2$ (0.41 g; 1.26 mmol). After a reaction time of 12 hours, the solvent is removed under reduced pressure and the residue is extracted with pentane. The filtrate is evaporated to dryness and the compound C is obtained in a yield of 78%.

$^1$H NMR (200 MHz, C$_4$D$_8$O): 7.8–6.9 (m, 4H, arom. H); 6.7–5.9 (m, 4H, Cp-H); 5.0; 4.9 (each m, each 1H, CH); 2.3 (s, 3H, CH$_3$).

EXAMPLE 5

(tert-Butyl-$\eta^3$-amidato)-$\eta^5$-cyclopentadienyl)-1,1-vinylidenediyl-zirconium bis(diethylamide)

At –20° C., 308 mg (1.99 mmol) of N-6-(6'-methylfulvenyl)pivalamide in 20 ml of diethyl ether are admixed with 2 equivalents of lithium hexamethyldisilazide and the mixture is stirred further for 4 hours at room temperature. The solid formed is filtered off and washed with 10 ml of diethyl ether and with 20 ml of pentane. After drying under reduced pressure, the dilithium salt obtained is suspended in 30 ml of THF and admixed with 1 equivalent of dichlorobis(diethylamido)zirconium (solution in 30 ml of THF) and the mixture is stirred further for 2 hours at room temperature. The solvent is removed under reduced pressure and the residue is stirred up with pentane. After filtering and taking off the solvent, the complex is obtained in a yield of 70%.

$^1$H-NMR (200 MHz, $C_6D_6$): 5.97 (m, 1H), 5.90 (m, 1H), 5.25 (d, 1H, 1.58 Hz), 5.00 (d, 1H, 1.58 Hz), 3.12 (q, 8 H, 7.42 Hz), 1.38 (s, 9H), 0.88 (tr, 12H, 7.42 Hz)

EXAMPLE 6

(p-Tolyl-$\eta^3$-amidato)-$\eta^5$-cyclopentadienyl)-1,1-vinylidenediyl-zirconium bis(diethylamide)

N-6-(6'-Methylfulvenyl)-p-toluamide is reacted using a method similar to Example 5. The complex is obtained in a yield of 65%.

$^1$H-NMR (200 MHz, $C_4D_8O$): 7.96 (d, 2H), 7.11 (d, 2H), 6.39 (m, 2H), 6.07 (m, 2H), 4.82 (d, 1H, 2.20 Hz), 4.80 (d, 1H, 2.23 Hz), 3.30 (q, 4H, 6.96 Hz), 3.29 (q, 4H, 6.96 Hz), 2.33 (s, 3H), 1.01 (t, 12H, 6.93 Hz).

What is claimed is:

1. A process for preparing an olefin polymer by polymerization of one or more olefins in the presence of the catalyst which comprises the combination of
   a) at least one transition metal compound and
   b) at least one cocatalyst
   wherein said transition metal compound is of the formula I

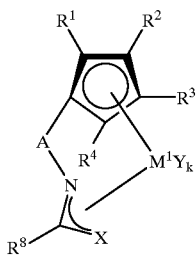

I where $M^1$ is a metal of group IIIb, IVb or Vb of the Periodic Table of the Elements, $R^1$, $R^2$, $R^3$ and $R^4$ are identical or different and are each a hydrogen atom, a halogen atom, a $C_1$–$C_{40}$-hydrocarbon-containing group, an —$SiR^5{}_3$, —$NR^5{}_2$, —$Si(OR^5)_3$, —$Si(SR^5)_3$ or —$PR^5{}_2$ radical, where $R^5$ are identical or different and are each a halogen atom, a $C_1$–$C_{10}$-alkyl group or a $C_6$–$C_{10}$-aryl group, or two or more radicals $R^1$, $R^2$, $R^3$ or $R^4$ together with the atoms connecting them form a ring system, Y are identical or different and are each a hydrogen atom, a $C_1$–$C_{40}$-hydrocarbon-containing group, an OH group, a halogen atom or an $NR^5{}_2$ group, where $R^5$ are identical or different and are each a halogen atom, a $C_1$–$C_{10}$-alkyl group or a $C_6$–$C_{10}$-aryl group, k is an integer which corresponds to the valence of the transition metal atom $M^1$ minus two and if Y is a butadiene unit, k is 1, A is a bridge, $R^8$ is a hydrogen atom, a halogen atom, a $C_1$–$C_{40}$-group, an —$SiR^5{}_3$, —$NR^5{}_2$, —$Si(OR^5)_3$, —$Si(SR^5)_3$ or —$PR^5{}_2$ radical, where $R^5$ are identical or different and are each a halogen atom, a $C_1$–$C_{10}$-alkyl group or a $C_6$–$C_{10}$-aryl group, and X is an element of group Va or VIa of the Periodic Table of the Elements, where if X is an element of group Va, X bears a radical $R^9$ which is a hydrogen atom, a halogen atom, a $C_1$–$C_{40}$-group, an —$SiR^5{}_3$, —$NR^5{}_2$, —$Si(OR^5)_3$, —$Si(SR^5)_3$ or —$PR^5{}_2$ radical, where $R^5$ are identical or different and are each a halogen atom, a $C_1$–$C_{10}$-alkyl group or a $C_6$–$C_{10}$-aryl group.

2. The process as claimed in claim 1, wherein said at least one cocatalyst is an aluminoxane or an aluminum alkyl or a mixture thereof.

3. The process as claimed in claim 2, wherein said aluminoxane is of the formula Xa for the linear type and/or the formula Xb for the cyclic type,

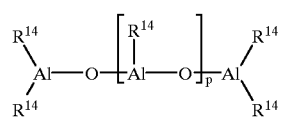

(Xa)

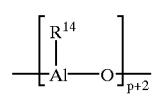

(Xb)

where, in the formulae Xa and Xb, the radicals $R^{14}$ are identical or different and are each hydrogen or a $C_1$–$C_{20}$-hydrocarbon group and p is an integer from 2 to 50.

4. The process as claimed in claim 3, wherein the radicals $R^{14}$ are identical and are hydrogen, methyl, isobutyl, phenyl or benzyl.

5. The process as claimed in claim 1, wherein
$M^1$ is a metal of group IVb of the Periodic Table of the Elements, $R^1$, $R^2$, $R^3$ and $R^4$ are identical or different and are each a hydrogen atom or a $C_1$–$C_{10}$-hydrocarbon-containing group or two or more radicals $R^1$, $R^2$, $R^3$ or $R^4$ together with the atoms connecting them form a ring system, Y are identical and are each a $C_1$–$C_{10}$-hydrocarbon-containing group or a halogen atom, A is

where n is an integer from 1 to 8, $R^6$ and $R^7$ are identical or different and are each a hydrogen atom or a $C_1$–$C_{10}$-hydrocarbon-containing group or in each case two radicals $R^6$, in each case two radicals $R^7$, or one of each of the radicals $R^6$ and $R^7$ in each case together with the atoms connecting them form a hydrocarbon ring system, $R^8$ is a $C_1$–$C_{10}$-hydrocarbon group, and X is an element of group Va or group VIa of the Periodic Table of the Elements, where if X is an element of group Va, X bears a radical $R^9$ which is a hydrogen atom or a $C_1$–$C_{10}$-hydrocarbon-containing group, or an —$SiR^5_3$, —$NR^5_2$, —$Si(OR^5)_3$, —$Si(SR^5)_3$ or —$PR^5_2$ radical, where $R^5$ are identical or different and are each a $C_1$–$C_{10}$-alkyl group or a $C_6$–$C_{10}$-aryl group.

6. The process as claimed in claim 5, wherein $M^1$ is titanium or zirconium, $R^1$, $R^2$, $R^3$ and $R^4$ are identical or different and are each a hydrogen atom, a $C_1$–$C_4$-alkyl group or a $C_6$–$C_{10}$-aryl group, or $R^1$ and $R^2$ or $R^3$ and $R^4$ or $R^2$ and $R^3$ together with the atoms connecting them form an aromatic hydrocarbon ring system, Y are identical and are methyl, phenyl or chlorine, A is

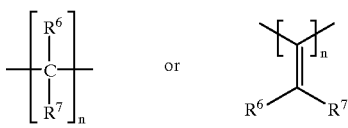

where $R^6$ and $R^7$ are identical or different and are each a hydrogen atom, a $C_1$–$C_4$-alkyl group or a $C_6$–$C_{10}$-aryl group, $R^8$ is a $C_1$–$C_4$-alkyl group or a $C_6$–$C_{10}$-aryl group, X is nitrogen or oxygen, where if X is nitrogen it bears a radical $R^9$ which is a hydrogen atom, a $C_1$–$C_4$-alkyl group, a $C_6$–$C_{10}$-aryl group, —$SiR^5_3$ or —$Si(OR^5)_3$, where $R^5$ are identical or different and are each a $C_1$–$C_4$-alkyl group or a $C_6$–$C_{10}$-aryl group.

7. The process as claimed in claim 1, wherein said catalyst is a supported catalyst.

8. The process as claimed in claim 1, wherein n is 1, 2, 3 or 4 and $R^1$ and $R^2$, or $R^3$ and $R^4$, or $R^2$ and $R^3$ together with the atoms connecting them form a six membered aromatic ring which optionally is substituted.

9. The process as claimed in claim 1, wherein the compound of formula I is selected from the group consisting of (tert-butyl-$\eta^3$-amidato)-($\eta^5$-cyclopentadienyl)-2,2-propanediyl-zirconium dichloride, (phenyl-$\eta^3$-amidato)-($\eta^5$-cyclopentadienyl)-2,2-propanediyl-zirconium dichloride,
(methyl-$\eta^3$-amidato)-($\eta^5$-cyclopentadienyl)-2,2-propanediyl-zirconium dichloride,
(tert-butyl-$\eta^3$-amidato)-($\eta^5$-cyclopentadienyl)-2-phenyl-2,2-ethanediyl-titanium dichloride,
(phenyl-$\eta^3$-amidato)-($\eta^5$-cyclopentadienyl)-2-phenyl-2,2-ethanediyl-titanium dichloride,
(methyl-$\eta^3$-amidato)-($\eta^5$-cyclopentadienyl)-2-phenyl-2,2-ethanediyl-titanium dichloride,
(tert-butyl-$\eta^3$-amidato)-($\eta^5$-cyclopentadienyl)-2,2-ethenediyl-zirconium dichloride,
(phenyl-$\eta^3$-amidato)-($\eta^5$-cyclopentadienyl)-2,2-ethenediyl-zirconium dichloride,
(methyl-$\eta^3$-amidato)-($\eta^5$-cyclopentadienyl)-2,2-ethenediyl-zirconium dichloride,
(p-tolyl-$\eta^3$-amidato)-($\eta^5$-cyclopentadienyl)-2,2-ethenediyl-zirconium dichloride,
(p-tolyl-$\eta^3$-amidato)-($\eta^5$-cyclopentadienyl)-2,2-ethenediyl-titanium dichloride,
(tert-butyl-$\eta^3$-amidato)-($\eta^5$-indenyl)-2,2-propanediyl-zirconium dichloride,
(phenyl-$\eta^3$-amidato)-($\eta^5$-indenyl)-2-phenyl-2,2-ethanediyl-zirconium dichloride,
(methyl-$\eta^3$-amidato)-($\eta^5$-indenyl)-2,2-propanediyl-titanium dichloride,
(tert-butyl-$\eta^3$-amidato)-($\eta^5$-3-methylcyclopentadienyl)-2-phenyl-2,2-ethanediyl-titanium dichloride,
(phenyl-$\eta^3$-amidato)-($\eta^5$-3-methylcyclopentadienyl)-2-phenyl-2,2-ethanediyl-zirconium dichloride,
(methyl-$\eta^3$-amidato)-($\eta^5$-3-methylcyclopentadienyl)-2,2-propanediyl-titanium dichloride,
(tert-butyl-N-methyl-$\eta^3$-amidinato)-($\eta^5$-cyclopentadienyl)-2,2-propanediyl-zirconium dichloride,
(phenyl-N-phenyl-$\eta^3$-amidinato)-($\eta^5$-cyclopentadienyl)-2,2-propanediyl-zirconium dichloride,
(methyl-N-trimethylsilyl-$\eta^3$-amidinato)-($\eta^5$-cyclopentadienyl)-2,2-propanediyl-zirconium dichloride,
(tert-butyl-N-methyl-$\eta^3$-amidinato)-($\eta^5$-cyclopentadienyl)-2-phenyl-2,2-ethanediyl-titanium dichloride,
(phenyl-N-trimethylsilyl-$\eta^3$-amidinato)-($\eta^5$-cyclopentadienyl)-2-phenyl-2,2-ethanediyl-titanium dichloride,
(methyl-N-phenyl-$\eta^3$-amidinato)-($\eta^5$-cyclopentadienyl)-2-phenyl-2,2-ethanediyl-titanium dichloride,
(tert-butyl-N-methyl-$\eta^3$-amidinato)-($\eta^5$-cyclopentadienyl)-2,2-ethenediyl-zirconium dichloride,
(phenyl-N-phenyl-$\eta^3$-amidinato)-($\eta^5$-cyclopentadienyl)-2,2-ethenediyl-zirconium dichloride,
(methyl-N-trimethylsilyl-$\eta^3$-amidinato)-($\eta^5$-cyclopentadienyl)-2,2-ethenediyl-zirconium dichloride,
(tert-butyl-N-trimethylsilyl-$\eta^3$-amidinato)-($\eta^5$-indenyl)-2,2-propanediyl-zirconium dichloride,
(phenyl-N-methyl-$\eta^3$-amidinato)-($\eta^5$-indenyl)-2-phenyl-2,2-ethanediyl-zirconium dichloride,
(methyl-N-phenyl-$\eta^3$-amidinato)-($\eta^5$-indenyl)-2,2-propanediyl-titanium dichloride,
(tert-butyl-$\eta^3$-amidinato)-($\eta^5$-3-methylcyclopentadienyl)-2-phenyl-2,2-ethanediyl-titanium dichloride,
(phenyl-$\eta^3$-amidinato)-($\eta^5$-3-methylcyclopentadienyl)-2-phenyl-2,2-ethanediyl-zirconium dichloride,
(methyl-$\eta^3$-amidinato)-($\eta^5$-3-methylcyclopentadienyl)-2,2-propanediyl-titanium dichloride,
(tert-butyl-$\eta^3$-amidato)-($\eta^5$-fluorenyl)-2,2-propanediyl-zirconium dichloride,
(phenyl-$\eta^3$-amidato)-($\eta^5$-fluorenyl)-2-phenyl-2,2-ethanediyl-titanium dichloride,
(methyl-$\eta^3$-amidato)-($\eta^5$-fluorenyl)-2,2-ethenediyl-zirconium dichloride,
(tert-butyl-N-methyl-$\eta^3$-amidinato)-($\eta^5$-fluorenyl)-2,2-propanediyl-zirconium dichloride,
(phenyl-N-trimethylsilyl-$\eta^3$-amidinato)-($\eta^5$-fluorenyl)-2-phenyl-2,2-ethanediyl-titanium dichloride,
(methyl-N-trimethylsilyl-$\eta^3$-amidinato)-($\eta^5$-fluorenyl)-2,2-ethenediyl-zirconium dichloride,
{(tert-butyl-$\eta^3$-amidato)(dimethyl)($\eta^5$-fluorenyl)silanediyl}zirconium dichloride,
{(phenyl-$\eta^3$-amidato)(methylphenyl)($\eta^5$-cyclopentadienyl)silanediyl)}zirconium dichloride,
{(methyl-$\eta^3$-amidato)(diphenyl)($\eta^5$-indenyl)silanediyl}]zirconium dichloride,
{(tert-butyl-N-methyl-$\eta^3$-amidinato)(dimethyl)($\eta^5$-cyclopentadienyl)silanediyl}zirconium dichloride,
{(phenyl-N-trimethylsilyl-$\eta^3$-amidinato)(methylphenyl)($\eta^5$-indenyl)silanediyl}zirconium dichloride,
{(methyl-N-trimethylsilyl-$\eta^3$-amidinato)(diphenyl)($\eta^5$-fluorenyl)silanediyl}zirconium dichloride,
(tert-butyl-$\eta^3$-amidato)-$\eta^5$-cyclopentadienyl)-1,1-vinylidenediyl-zirconium bis(diethylamide), (tert-butyl-η³-amidato)-η⁵-cyclopentadienyl)-1,1-vinylidenediyl-zirconium bis(dimethylamide) and
(p-tolyl-η³-amidato)-η⁵-cyclopentadienyl)-1,1-vinylidenediyl-zirconium bis(diethylamide).

10. The process as claimed in claim 9, wherein said at least one cocatalyst is an aluminoxane or an aluminum alkyl or a mixture thereof.

11. The process as claimed in claim 10, wherein said aluminoxane is of the formula Xa for the linear type and/or the formula Xb for the cyclic type,

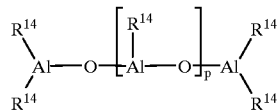

(Xa)

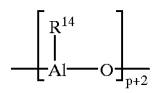

(Xb)

where, in the formulae Xa and Xb, the radicals $R^{14}$ are identical or different and are each hydrogen or a $C_1$–$C_{20}$-hydrocarbon group and p is an integer from 2 to 50.

12. The process as claimed in claim 11, wherein the radicals $R^{14}$ are identical and are hydrogen, methyl, isobutyl, phenyl or benzyl.

13. The process claimed in claim 1, wherein A is

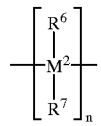 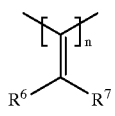 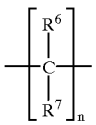

-continued

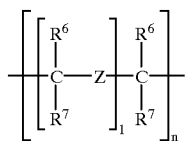 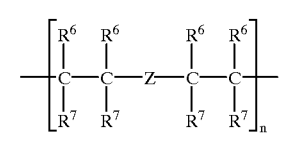

where n is an integer from 1 to 20, l is an integer from 1 to 20,

Z is

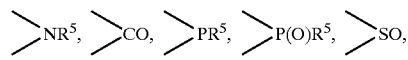

$SO_2$, O or S, where $R^5$ are identical or different and are each a halogen atom, a $C_1$–$C_{10}$-alkyl group or a $C_6$–$C_{10}$-aryl group, $R^6$ and $R^7$ are identical or different and are each a hydrogen atom, a halogen atom, a $C_1$–$C_{40}$-hydrocarbon-containing group or in each case two radicals $R^6$, in each case two radicals $R^7$, or one of each of the radicals $R^6$ and $R^7$ in each case together with the atoms connecting them form a ring system and $M^2$ is silicon, germanium or tin, $M^1$ is a metal of group IVb of the Periodic Table of the Elements, $R^1$, $R^2$, $R^3$ and $R^4$ are identical or different and are each a hydrogen atom or a $C_1$–$C_{10}$-hydrocarbon-containing group or two or more radicals $R^1$, $R^2$, $R^3$ or $R^4$ together with the atoms connecting them form a ring system, Y are identical and are each a $C_1$–$C_{10}$-hydrocarbon-containing group or a halogen atom.

* * * * *